US006908946B2

(12) United States Patent
Cook et al.

(10) Patent No.: US 6,908,946 B2
(45) Date of Patent: Jun. 21, 2005

(54) CONJUGATED NONADECADIENOIC ACID COMPOSITIONS

(75) Inventors: Mark E. Cook, Madison, WI (US);
Michael W Pariza, Madison, WI (US);
Yeonhwa Park, Madison, WI (US);
Guangming Li, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 334 days.

(21) Appl. No.: 10/161,476

(22) Filed: May 31, 2002

(65) Prior Publication Data

US 2003/0008845 A1 Jan. 9, 2003

Related U.S. Application Data

(60) Provisional application No. 60/294,908, filed on May 31, 2001, and provisional application No. 60/362,248, filed on Mar. 6, 2002.

(51) Int. Cl.[7] .............................................. A61K 31/20
(52) U.S. Cl. ..................................................... 514/560
(58) Field of Search ........................................ 514/560

(56) References Cited

U.S. PATENT DOCUMENTS

| | | | | |
|---|---|---|---|---|
| 5,855,917 A | * | 1/1999 | Cook et al. ................... | 424/502 |
| 6,060,304 A | * | 5/2000 | Pariza et al. .............. | 435/252.9 |
| 6,126,960 A | * | 10/2000 | Nilsen et al. ................ | 424/440 |
| 6,184,009 B1 | * | 2/2001 | Cain et al. ................... | 435/134 |
| 6,316,645 B1 | * | 11/2001 | Sih et al. ..................... | 554/126 |
| 6,555,579 B2 | * | 4/2003 | Kritchevsky ................. | 514/560 |
| 2003/0091654 A1 | * | 5/2003 | Katz et al. ................... | 424/655 |

FOREIGN PATENT DOCUMENTS

| | | |
|---|---|---|
| WO | WO 98/09621 | 3/1998 |
| WO | WO 01/17526 | 3/2001 |

OTHER PUBLICATIONS

Park et al. Lipids, vol. 32, No. 8 (1997) pp853–858.*
Carballeira NM, et al., Facile syntheses for (5Z,(9Z)–5, 9–hexadecadienoic acid, (5Z,9Z)–5,9–nonadecadienoic acid, and (5Z,9Z)–5,9–eicosadienoic acid through a common synthetic route. Chem Phys Lipids. 1999 Jul;100(1–2):33–40.

Carballeira NM, et al., 5,9–Nonadecadienoic acids in malvaviscus arboreus and allamanda cathartica. Phytochemistry. 1998 Nov;49(5):1253–1256.

Mizushina Y, et al., The inhibitory action 14,15 of fatty acids on DNA polymerase beta. Biochemica et Biophysica Acta. 1997 Oct;1336(3):509–521.

Pariza, MW, et al., The biologically active isomers of conjugated linoleic acid. Prog Lipid Res. 2001 Jul;40(4):283–98.

Database WPI, Section Ch, Week 198421, Derwent Publications Ltd., London, GB; 1994 Apr.

Beerthuis et al., "Synthesis of a Series of Polyunsaturated Fatty Acids, Their Potencies as Essential Fatty Acids and as Precursors of Prostaglandins", Recl. Trav. Chim. Pavs–Bas 90:943–960 (1971).

Fretland et al., "The Long Duration in vivo, Inhibition of Prostaglandin Synthetase by 2–Methyl–8CIS–12–Trans–14–CIS–Eicosatrien Oic Acid", Biochem. Pharmacol. 34 (12):2103–2107 (1985).

Nugteren, D.H., "Inhibition of Prostaglandin Biosynthesis by 8CIS, 12Trans, 14CIS–Eicosatrienoic Acid and 5CIS, 8CIS, 12 Trans, 14CIS Eicosatetraenoic Acid", Biochim. Biophys. Acta 210(1):171–176 (1970).

Nugteren et al., "Naturally Occurring Conjugated Octadecatrienoic Acids are Strong Inhibitors of Prostaglandin Biosythesis", Prostaglandins 33(3):403–417 (1987).

* cited by examiner

*Primary Examiner*—Raymond J. Henley, III
(74) *Attorney, Agent, or Firm*—Quarles & Brady LLP

(57) ABSTRACT

The present invention provides a method of using conjugated nonadecadienoic acid (CNA), one of its derivatives, or a combination thereof to inhibit lipoprotein lipase activity associated with a cell, to control body fat in a human or non-human animal, to inhibit cyclooxygenase activity in a cell, to inhibit platelet aggregation in a human or non-human animal, and to prevent or treat a condition or disease related to platelet aggregation.

12 Claims, 7 Drawing Sheets

CONJUGATED NONADECADIENOIC ACID COMPOSITIONS

CROSS-REFERENCE TO RELATED APPLICATION

This application claims the benefit of U.S. provisional applications bearing Ser. No. 60/294,908, filed on May 31, 2001, and Ser. No. 60/362,248, filed on Mar. 6, 2002.

STATEMENT REGARDING FEDERALLY SPONSORED RESEARCH OR DEVELOPMENT

To be determined.

BACKGROUND OF THE INVENTION

It can be desirable in the medical and veterinary arts to reduce fat accumulation in fat-storing cells ("adipocytes"). In obese human and non-human animals in particular, adipocytes that accumulate excess lipids can become insulin-resistant, a characteristic that has many adverse effects including the development of diabetes. Adipocytes cannot directly take up and accumulate triglycerides from the blood. Instead, an cell-associated extracellular lipoprotein lipase (LPL) enzyme breaks down blood-borne triglyceride molecules into a glycerol molecule and three fatty acids molecules. The adipocytes can take up and convert the fatty acids into triacylglycerides for accumulation and storage.

Likewise, adipocytes cannot directly secrete fatty acids. Instead, a intracellular hormone-sensitive lipase breaks down cellular triacylglycerides into free fatty acid and glycerol metabolites that can be released from the cells. Hormone-sensitive lipase activity increases and decreases in response to its phosphorylation by a cyclic AMP-dependent protein kinase. The extent of phosphorylation, in turn, is determined by cyclic AMP levels. Norepinephrine and glucagon stimulate cyclic AMP production while insulin decreases cyclic AMP levels.

Conjugated linoleic acid (CLA), a series of positional and geometric isomers having eighteen carbons and a pair of conjugated double bonds, has many biological activities including those related to the metabolism of body fat and arachidonic acid. CLA inhibits LPL activity and prevents fat accumulation in human and non-human animals. Other compounds and methods for controlling body fat by reducing accumulation of fat in fat cells are desired.

CLA also inhibits platelet aggregation, in that it inhibits cyclooxygenase (COX)-directed conversion of arachidonic acid to prostaglandins and thromboxanes. Thromboxane A2 is a potent inducer of platelet aggregation. Inhibition of platelet aggregation advantageously reduces the risk of arteriosclerosis, inflammation, and risk of stroke. Millions of Americans are prescribed aspirin to reduce the risk of these diseases. Other compounds and methods for inhibiting platelet aggregation are also desired.

BRIEF SUMMARY OF THE INVENTION

The present invention provides a method for inhibiting adipocyte-associated lipoprotein lipase activity in a human or non-human animal by administering a treating agent that comprises at least one of conjugated nonadecadienoic acid (CNA) and at least one derivative thereof in an amount effective to modulate the lipoprotein lipase activity. As a result, body fat is controlled, cyclooxygenase activity is inhibited or platelet aggregation is inhibited in the animal, thereby preventing or treating a related condition or disease.

The present invention also provides an edible composition comprising at least one of CNA and at least one derivative thereof in an amount effective to modulate the lipoprotein lipase activity, with an edible carrier.

The present invention also provides a pharmaceutical composition comprising at least one of CNA and at least one derivative thereof in an amount effective to modulate the lipoprotein lipase activity, with a pharmaceutical carrier.

It is an object of the present invention to provide compositions and methods for controlling body fat, inhibiting cyclooxygenase activity, reducing release of PGE2, and inhibiting platelet aggregation in a cell of a human or non-human animal.

Other objects, features, and advantages of the invention will be apparent upon consideration of the following detailed description taken in conjunction with the accompanying drawings.

DETAILED DESCRIPTION OF THE INVENTION

Figure 1:
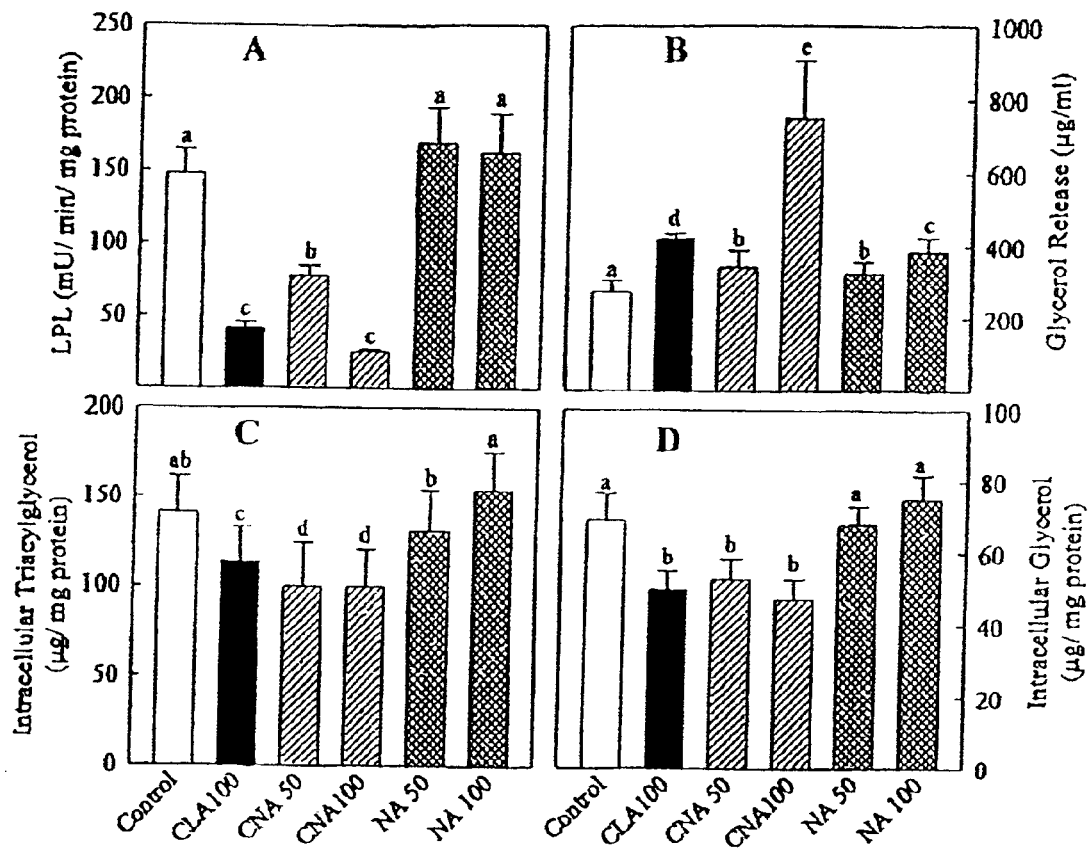
FIG. 1 shows effects of CNA and CLA on LPL activity (A), glycerol release (B), cellular triacylglycerol (C), and cellular glycerol (D) in 3T3-L1 adipocytes.

The applicants here disclose biological activities of CNA related to the metabolism of body fat and arachidonic acid. In particular, CNA modulates adipocyte-associated LPL activity and controls body fat levels in human and non-human animals when administered in sufficient quantity. Further, CNA inhibits cyclooxygenase 1 (COX 1) activity and cyclooxygenase 2 (COX 2) activity as well as thromboxane B2 formation and platelet aggregation in the blood of human and non-human animals when administered in sufficient quantity.

CNA is a 19 carbon free fatty acid having a pair of conjugated double bonds. CNA can be prepared by alkali isomerization of c10, c13 nonadecadienoic acid (NA, commercially available from Nu-Chek Prep, Elysian, Minn.), using the method described for preparing CLA by Y. Park et al., *Lipids* 34 (1999) 235–241, incorporated herein by reference as if set forth in its entirety. CNA can also be prepared using the methods of Janssen, G., et al., "Location of Double Bonds in Polyenic Long-Chain Carboxylic Acids Containing a Conjugated Diene Unit," *Biomedical and Environmental Mas Spectrometry* 15:1–6 (1988) and Verhulst, A., et al., "Isolation of Polyunsaturated Long Chain Fatty Acids by Propionibacteria," *Systematic and Applied Microbiology* 9:12–15 (1987), each incorporated herein by reference as if set forth in its entirety. CNA isomers of interest for use in the method include t11, c13 CNA and c10, t12 CNA.

The treating agent comprises at least one of CNA and at least one CNA derivative. A CNA derivative is preferred over CNA itself as a component of edible and pharmaceutical compositions. A CNA derivative is preferably an ester, phospholipid or salt of CNA. Preferred esters are a glyceride, a methyl ester and an ethyl ester. Still more preferably, the preferred glyceride is a triglyceride, diglyceride, or monoglyceride of CNA. Methods for preparing triglycerides, diglycerides, monoglycerides, phospholipids and salts from free fatty acids are known in the art. A method of making triglycerides from fatty acids can be found in *Journal of General Chemistry*, USSR, 34: 1918, 1964, incorporated by reference herein as if set forth in its entirety. Briefly in this method, methyl esters of fatty acids are mixed with triacetin and sodium methoxide. The mixture is heated in an oil bath at 80° C. for five hours and fatty acid triglycerides are obtained. Alternatively, free CNA can be fed to an animal. The animal esterifies CNA and the esters (phospholipids, triglycerides, diglycerides and monoglycerides) can be extracted from the blood and separated using methods known in the art. Still another method for making CNA in triglyceride form is the method used in connection with CLA in U.S. Pat. No. 6,177,580, incorporated herein by reference as if set forth in its entirety. CNA metabolites are structurally distinct from those of CLA.

Examples of methods for preparing phospholipids from fatty acids are found in the following references, each of which is incorporated herein by reference as if set forth in its entirety: Babaev, et al., Mater. Vegs. Simp. (1981) Meeting Date 1980, 62–9; Bilimoria, et al, J. Chem. Soc. (1968) (12) 1404–12; Bonsen, et al., Chem. Phys. Lipids (1967) 1(2) 100–9; Isaacson, et al., Chem. Phys. Lipids (1990) 52(3–4) 217–26; Smith, et al., Tech. Life Sci., [Sect.]: Biochem. (1982) 8406; and Zhu et al., Journal of Chemical Research, Synopses (1999)(8) 500–501.

CNA salts can be made using the method for making CLA salts described in U.S. Pat. No. 5,070,104, incorporated herein by reference as if set forth in its entirety, substituting CNA or derivative thereof for the CLA or derivative thereof in the patent. Lithium salts are particularly preferred.

In one embodiment, the present invention is a method of inhibiting activity of LPL associated with a cell. "LPL associated with a cell" is LPL located not inside but outside of the adipocyte cell. The method involves treating the cell with CNA, a CNA derivative, or a combination of either of the foregoing in an amount effective to inhibit the associated lipoprotein lipase activity. When treating an in vitro cultured cell, the treating agent can be added into the culture medium to a total concentration of CNA and/or derivatives thereof in the range of from about 10 $\mu$M to about 1,000 $\mu$M, preferably from about 30 $\mu$M to about 500 $\mu$M, and most preferably from about 50 $\mu$M to about 150 $\mu$M.

When treating a cell in a human or non-human animal, an amount of the treating agent effective to achieve an object of the invention is administered into the animal by, e.g., feeding, intravenous injection, topical treatment on skin, or direct injection into adipose tissue. The treatment can be applied to organs, as well—particularly organs harvested for transplant and having elevated cyclooxygenase enzyme. For convenience, feeding is a preferred administration route. When fed, the total amount of CNA and/or derivatives thereof in the treating agent can range from about 0.0001% to about 5% by weight in diet, preferably from about 0.05% to about 1% by weight in diet, and most preferably from about 0.1% to about 0.5% by weight in diet. One of ordinary skill in the art can readily measure the total concentration of these agents in the blood when different diets listed above are fed and determine the corresponding dose of these agents for intravenous injection. When administered directly into the adipose tissue, the concentration of these agents in the injection solution are the same as the concentration in the culture medium described above.

In another embodiment, the present invention is a method of controlling body fat in a human or non-human animal. Body fat control means is achieved when at least one of the following three effects is observed: the body fat level is reduced in the animal to a level lower than that just before CNA treatment; the body fat level is maintained in the animal at a level substantially the same as that just before CNA treatment wherein the body fat level was increasing before CNA treatment; and body fat level remains lower in the animal than it would have been without CNA treatment. The method involves administering CNA, a CNA derivative or a combination thereof into the animal. The administration routes and doses are as described above for inhibiting LPL activity.

In still another embodiment, the present invention is method of treating a cell to inhibit cyclooxygenase activity in the cell. By cyclooxygenase activity, we mean the activity of cyclooxygenase-1, cyclooxygenase-2, or both. The inhibition can arise by various means, including but not limited to altering the cyclooxygenase primary, secondary, tertiary or quaternary structure, by reducing or eliminating the cyclooxygenase, or by modifying transcription or translation of cyclooxygenase-encoding polynucleotides. The method involves treating the cell with CNA, a CNA derivative or a combination thereof. When treating an in vitro cultured cell, tissue or organ, the treating agent can be added into the culture medium to a total concentration of CNA and/or derivatives thereof in the range of from about 3 $\mu$M to about 1,000 $\mu$M, preferably from about 5 $\mu$M to about 500 $\mu$M, and most preferably from about 10 $\mu$M to about 300 $\mu$M.

When treating a cell of a human or non-human animal, an amount of the treating agent effective to achieve an object of the invention is administered into the animal by, e.g., feeding, intravenous injection, topical treatment of skin, or direct injection into adipose tissue. For convenience, feeding and topical administration are preferred administration routes when treating a cell in a human or non-human animal. Whether fed or injected intravenously, the total concentration of CNA and/or derivatives in the treating agent is adjusted such that after injection, the total concentration of CNA and/or derivatives in the blood ranges from 3 $\mu$M to about 1,000 $\mu$M, preferably from about 5 $\mu$M to about 500 $\mu$M, and most preferably from about 10 $\mu$M to about 300 $\mu$M. Given the stated blood concentration ranges, one of ordinary skill in the art can readily determine the dose to be administered.

In yet another embodiment, the present invention is a method of inhibiting platelet aggregation, or preventing or treating a condition or disease related to platelet aggregation in a human or non-human animal. Examples of conditions or diseases related to platelet aggregation include but are not limited to arteriosclerosis, inflammation and stroke. The method involves administering CNA, a CNA derivative or a combination thereof into the animal. Suitable administration routes and doses are as described above for inhibiting cyclooxygenase activity.

In another embodiment, the present invention is an edible composition suitable for consumption by a human or non-human animal, particularly for use in the disclosed methods. The composition contains CNA or a CNA derivative with an edible carrier of the type known to the art. The presence of the carrier should not unduly interfere with the activity of the CNA or CNA derivative in the methods of the invention. Thus, the carrier should not reduce the effect of the CNA or CNA derivative in a method by more than 20 percent. It is understood that if the carrier masks the activity in the methods, the amount of CNA or CNA derivative can be increased accordingly. It is understood that the edible compositions of the invention include foods having added thereto at least one of CNA and at least one CNA derivative. Particularly advantageous foods include food products that contain fatty acids such as dairy products and nutritional supplements.

In another embodiment, the present invention is a pharmaceutical composition suitable for administration to a human or non-human animal, particularly for use in the disclosed methods. The composition contains at least one of CNA or a CNA derivative with an pharmaceutical carrier of the type known to the art. The presence of the carrier should not unduly interfere with the activity of the CNA or CNA derivative in the methods of the invention. Thus, the carrier should not reduce the effect of the CNA or CNA derivative in a method by more than 20 percent. It is understood that if the carrier masks the activity in the methods, the amount of CNA or CNA derivative can be increased accordingly.

One of ordinary skill in the art is familiar with edible and pharmaceutical formulations that are suitable for human and non-human animal use.

The invention will be more fully understood upon consideration of the following non-limiting examples.

EXAMPLE 1

Effects of CNA and CLA on Heparin-releasable LPL Activity, Glycerol Release, Cellular Triacylglycerol, and Cellular Glycerol in 3T3-L1 Adipocytes Materials and Methods CNA was synthesized from NA (purchased from Nu-Chek Corp., Elysian, Minn.), using the method described in Park, Y. et al., *Lipids* 34 (1999) 235–241 for producing CLA from linoleic acid; the CNA product synthesized contained 97.3% CNA (c10, t12, 33.4%; t11, c13, 32.9%; t10, t12/t11, t13, 23.4%; other isomers, 7.6%) with the remainder as unreacted NA. CLA was synthesized as described by Park, et al., supra; the CLA product synthesized contained 97.8% CLA (c9, t11/t9, c11, 45.7%; t10, c12, 47.6%; t9, t11/t10, t12, 1.7%; others, 2.8%) with the remainder as unreacted linoleic acid.

Cultured cells were treated with fatty acid-albumin complexes for 2 days, beginning at day 6 post-differentiation. Data were analyzed as log value with a two-way ANOVA using fatty acid (as treatments) and experiment. If the interaction between treatment and experiment was significant, this interaction was used as the error term. Additional experimental details were as described in Park, et al., supra.

Results

Treatment values indicate the concentration of test materials ($\mu$M); all treatment groups included albumin at 100 $\mu$M. Reported values are mean±S.E. (n=8, collected from two independent experiments). Means with different letters are significantly different (P<0.05). CNA inhibited LPL activity in cultured 3T3-L1 adipocytes (FIG. 1A). In addition, CNA enhanced glycerol release (FIG. 1B) and reduced intracellular triacylglycerol (FIG. 1C) and glycerol (FIG. 1D) in the same cells. In contrast, NA at 50 or 100 $\mu$M was ineffective.

EXAMPLE 2

Effects of CNA on Body Composition

Materials and Methods

Female ICR mice (4-week-old) and semi-purified diets (TD94060, 99% basal mix) were purchased from Harlan Sprague Dawley (Madison, Wis.) and Harlan Teklad (Madison, Wis.), respectively. CLA was obtained from Natural Lipids Ltd AS, Hovdebygda, Norway; its composition was 88.7% CLA (c9, t11/t9, c11, 41.9%; t10, c12, 43.5%; t9, t11/t10, t12, 1.5%; others, 1.8%) with the remainder as oleic acid, 5.6%; palmitic acid, 1.4%; and linoleic acid, 0.5%. CNA was kindly provided by the US Food and Drug Administration; it was 98.6% CNA (c10, t12, 42.3%; t11, c13, 48.0%; t10, t12/t11, t13, 5.1%; others, 3.2%) with the remainder as unreacted NA. CLA or CNA was added to diets at the expense of corn oil to maintain 5.5% fat. Diet was stored at −20° C. until use. Mice were housed individually in a windowless room with a 12-h light-dark cycle in strict accordance to guidelines established by the Research Animal Resources Center of University of Wisconsin-Madison. Diet and water, available ad libitum, were freshly provided three times per week.

After a 5 day adaptation period, mice were randomly separated into 3 groups and fed control diet, diet supplemented with 0.3% CLA, or diet supplemented with 0.3% CNA for 2 weeks. 0.3% of diet CLA is a sub-optimal dose for CLA's effects on body composition.

Results

Results are mean±S.E. (n=6). Means with different letters in each column are significantly different (P<0.01 for water and fat, and P<0.05 for empty carcass weight (ECW), protein and ash).

Table 1 shows that a CNA diet in mice reduced body fat mass gain and enhanced the amount of whole body water, protein and ash. Feeding mice with CLA diet caused similar but less dramatic changes.

The CLA and CNA groups also displayed reductions in body weight gain and feed intake relative to controls during the experimental period. Body weight gain per animal for controls, CLA and CNA groups were 2.5 g, 1.3 g, 0.2 g, respectively; total feed intake per group for controls, CLA and CNA groups were 57.9 g, 51.0 g, 47.1 g, respectively. It has been repeatedly shown in CLA-feeding trials (see, e.g., Y. Park, et al., *Lipids* 34 (1999) 243–248) that these are transient effects that are sometimes but not always seen, and are unrelated to the observed changes in body composition.

TABLE 1

Effects of CNA and CLA on body composition.

|  | ECW (g) | % Fat | % Water | % Protein | % Ash |
|---|---|---|---|---|---|
| Control | $24.5^a \pm 0.7$ | $20.00^a \pm 2.28$ | $57.9^a \pm 1.7$ | $18.35^a \pm 0.61$ | $3.83^a \pm 0.15$ |
| CLA | $23.2^{ab} \pm 0.6$ | $14.98^a \pm 2.08$ | $59.9^a \pm 1.7$ | $19.16^a \pm 0.50$ | $4.01^{ab} \pm 0.13$ |
| CAN | $21.8^b \pm 0.4$ | $3.90^b \pm 0.44$ | $66.2^b \pm 0.4$ | $20.79^b \pm 0.24$ | $4.42^b \pm 0.12$ |

EXAMPLE 3

Effects of CNA on Platelet Aggregation, Thromboxane B2 Level, PGE2 Level, and COX-1 and COX-2 Activity Materials and Methods Female guinea pigs and diets were purchased from Harlan Teklad (Madison, Wis). Whole Blood Aggregometer, collagen and ADP were purchased from Chrono-log Corp. (Havertown, Pa.). All ELISA kits were purchased from Cayman Chemical (Ann Arbor, Mich.).

Whole blood platelet aggregation: Guinea Pigs were anesthetized with a combination of ketamine (35 mg/kg) and xylazine (10 mg/kg) by subcutaneous administration. Heparinized blood (20 unit/ml) was obtained by cardiac puncture. Within 5–10 minutes, the blood (1.0 ml) was preheated at 37° C. and then incubated with free fatty acid or DMSO (control) for 2 minutes. Collagen (4 µg/ml) or ADP (10 µM) was next added to the blood to start the platelet aggregation process. Platelet aggregation was measured using an Aggregometer.

Determination of thromboxane B2 level by ELISA: After the whole blood platelet aggregation, the collagen-stimulated blood was centrifuged for plasma and stored at −80° C. The plasma thromboxane level was determined by ELISA according to the manufacturer's instructions.

Inhibitory effects on ovine COX-1 and COX-2: COX-1 or COX-2, heme and reaction buffer were pre-incubated under 37° C. CNA or DMSO (control) was added to the system and co-incubated for 5 minutes. Arachidonic acid was added and the reaction was maintained at 37° C. for 2 minutes. The catalysis reaction was terminated by adding HCL. Total prostanoids were measured by ELISA according to manufacturer's instructions.

Results

Figure 2:
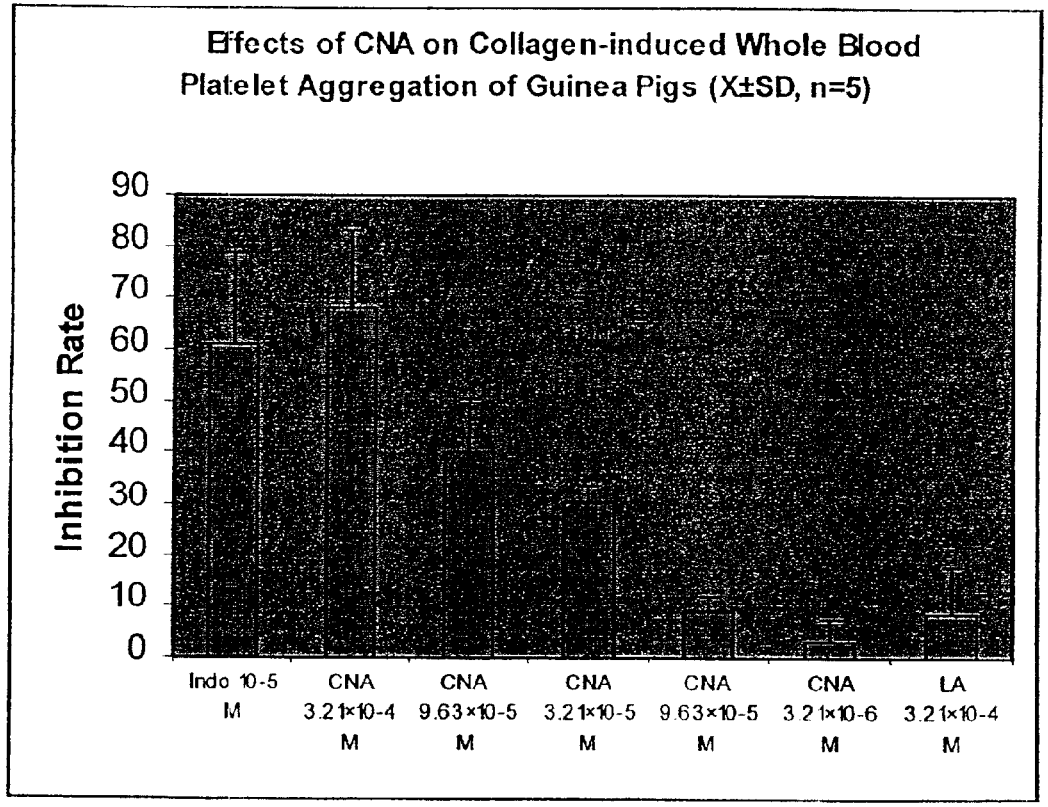
FIG. 2 shows effects of CNA on collagen-induced whole blood platelet aggregation of guinea pigs (mean±standard deviation, n=5).
Figure 3:
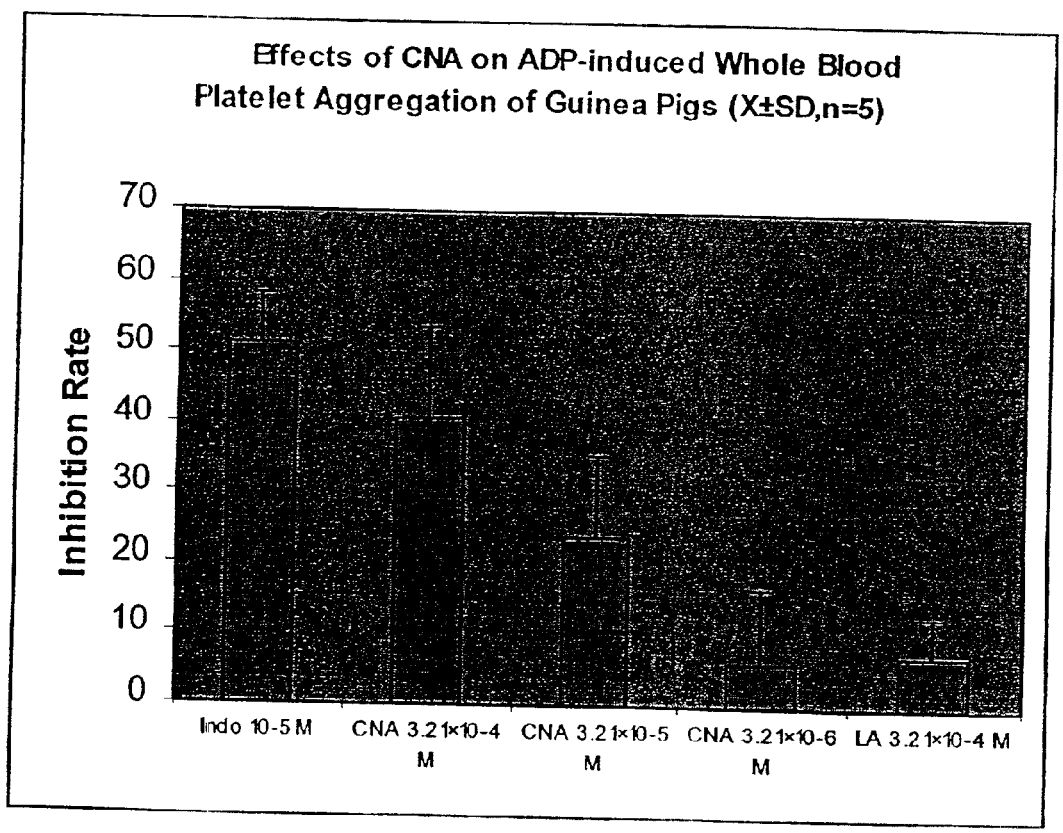
FIG. 3 shows effects of CNA on ADP-induced whole blood platelet aggregation of guinea pigs (mean±standard deviation, n=5).
Figure 4:
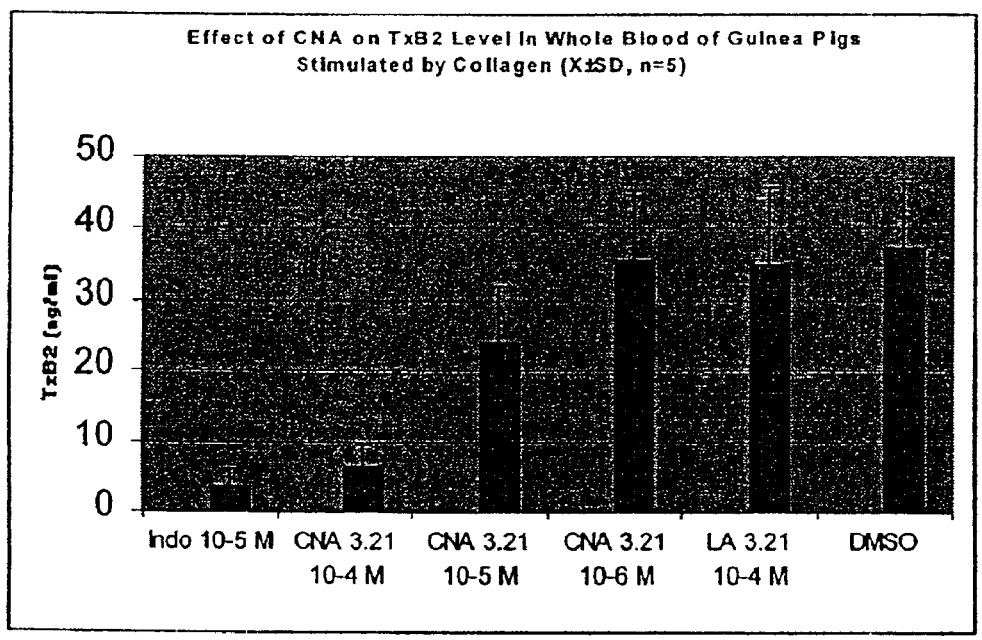
FIG. 4 shows effects of CNA on thromboxane B2 release in whole blood of guinea pigs stimulated by collagen (mean±standard deviation, n=5).
Figure 5:
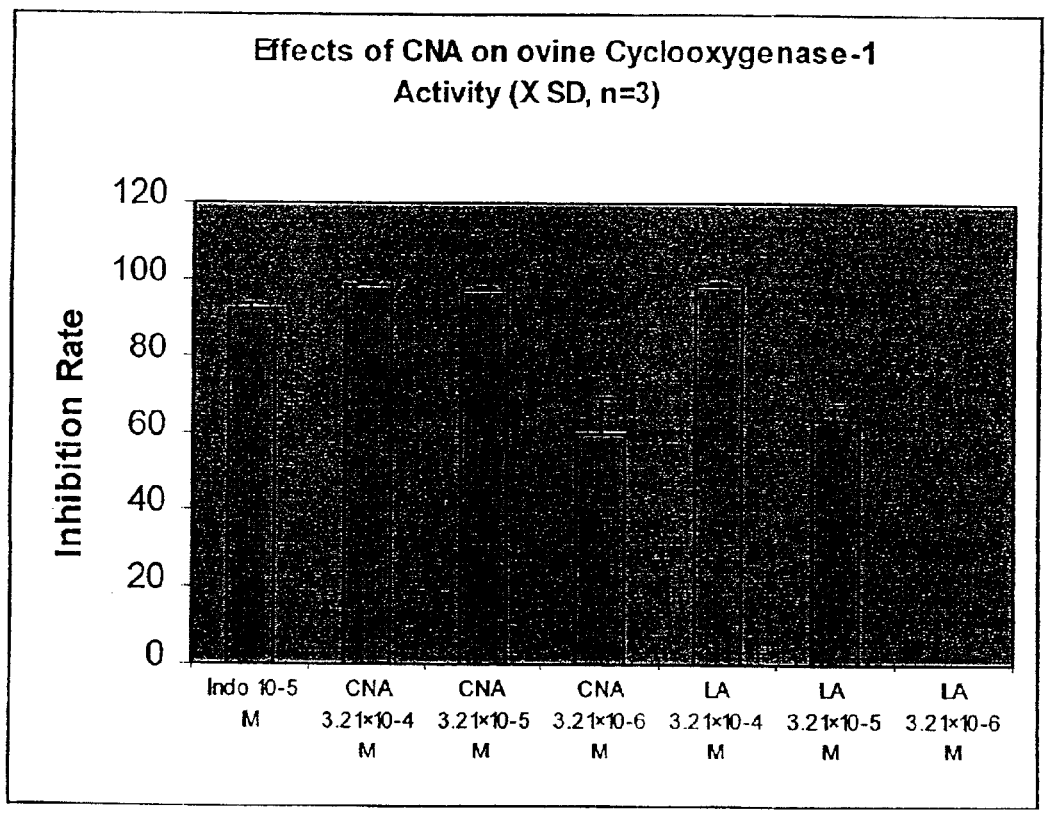
FIG. 5 shows effects of CNA on ovine cyclooxygenase-1 activity (mean±standard deviation, n=3).
Figure 6:
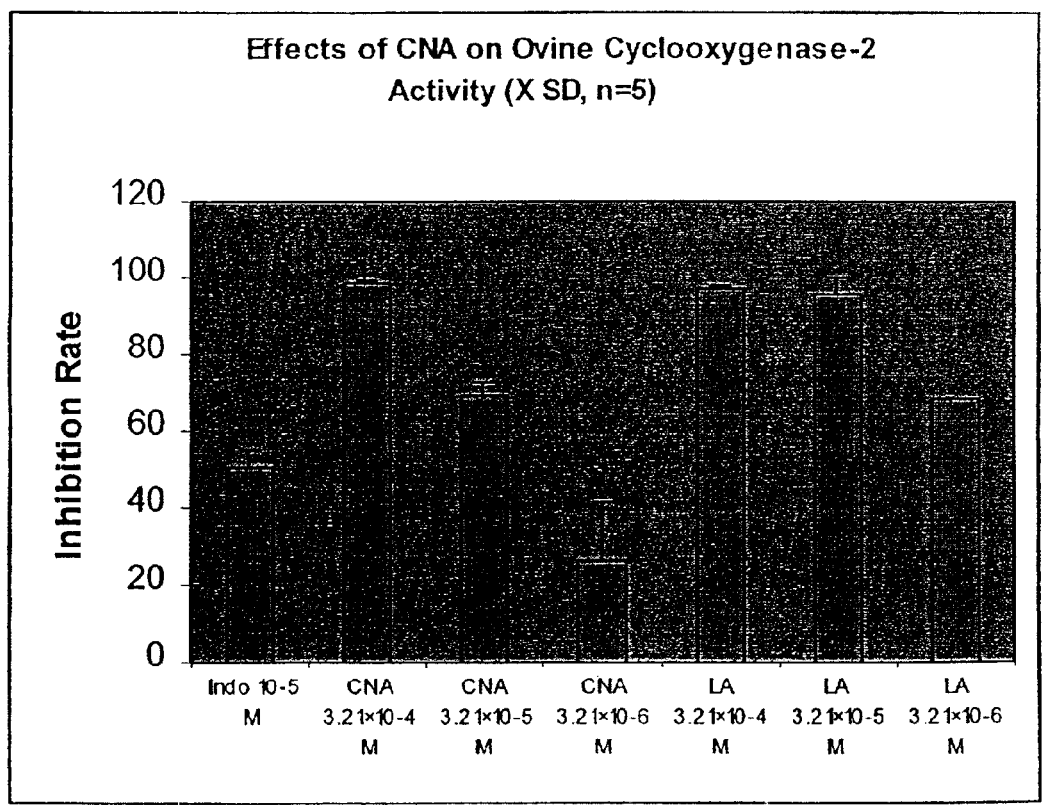
FIG. 6 shows effects of CNA on ovine cyclooxygenase-2 activity (mean±standard deviation, n=5).

CNA inhibited the collagen- and ADP-stimulated platelet aggregation in a dose-dependent manner (FIG. 2 and FIG. 3). CNA also reduced thromboxane B2 level in collagen-stimulated blood in a dose-dependent manner (FIG. 4). In addition, CNA inhibited pure ovine COX-1 and COX-2 in a dose-dependent manner (FIG. 5 and FIG. 6).

Figure 7:
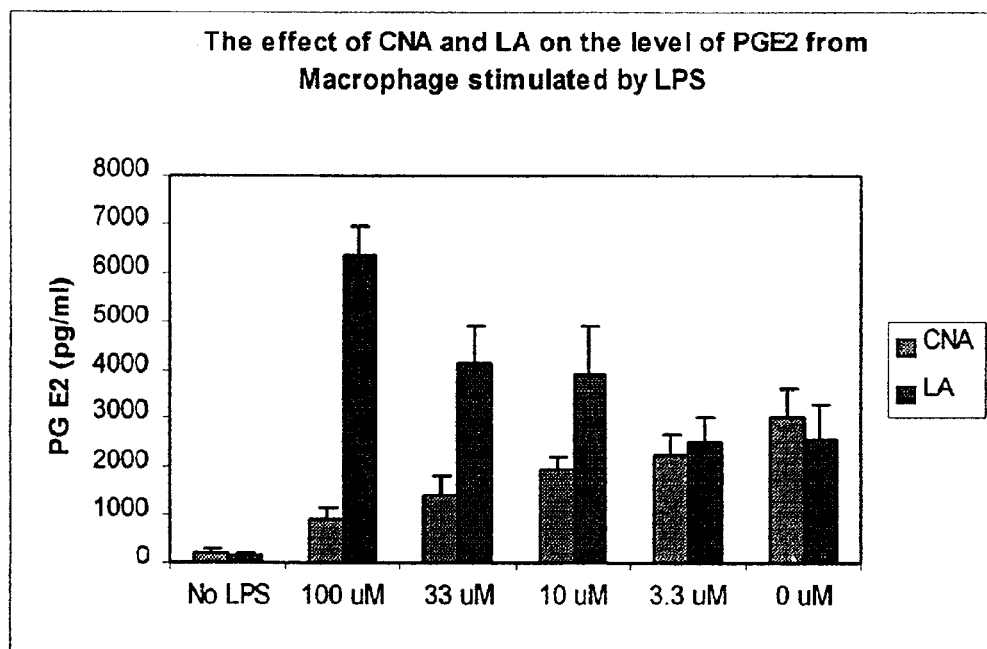
FIG. 7 depicts the inhibitory effects of CNA on lipopolysaccharide-stimulated macrophages.

As a further indication of the ability of CNA to inhibit COX enzymes, FIG. 7 depicts the inhibition of PGE2 released from stimulated macrophages in the presence of varying amounts of CNA. Confluent macrophages were incubated with CNA or linoleic acid (LA; control) at the concentrations shown for 24 hours in 0.5% fetal bovine serum then were stimulated with 100 ng/ml lipopolysaccharide (LPS) for 8 hours. The level of PGE2 in the medium was determined by ELISA assay. FIG. 7 shows substantial inhibition to less than 1000 pg/ml from a level of about 3000 pg/ml in LPS-stimulated macrophages without CNA.

The present invention is not intended to be limited to the foregoing examples, but encompasses all such modifications and variations as come within the scope of the appended claims.

We claim:

1. A method for modulating lipoprotein lipase activity associated with a cell, the method comprising the step of:
   administering to the cell a composition that comprises at least one treating agent comprising an isomer selected from the group consisting of cis-10, trans-12 conjugated nonadecadienoic acid (CNA), trans-11, cis-13 CNA, trans-10, trans-12 CNA, trans-11, trans-13 CNA and at least one derivative selected from the group consisting of an ester of CNA, a phospholipid of CNA and a salt of CNA of an above CNA isomer in an amount sufficient to modulate the lipoprotein lipase activity.

2. A method for modulating lipoprotein linase activity associated with an in vitro cultured cell, the method comprising the step of:
   administering to the cell a composition that comprises at least one treating agent selected from the group consisting of a conjugated nonadecadienoic acid (CNA) and at least one CNA derivative selected from the group consisting of an ester of CNA, a phospholipid of CNA and a salt of CNA in an amount sufficient to modulate the lipoprotein lipase activity.

3. The method of claim 1 wherein the cell is in a human or non-human animal.

4. The method of claim 1 or 2 wherein the ester of CNA is a glyceride.

5. The method of claim 4 wherein the glyceride is selected from the group consisting of a triglyceride of CNA, a diglyceride of CNA, and a monoglyceride of CNA.

6. A method for controlling body fat in a human or non-human animal, the method comprising the step of:
   administering a composition that comprises at least one treating agent comprising an isomer selected from the group consisting of cis-10, trans-12 conjugated nonadecadienoic acid (CNA), trans-11, cis-13 CNA, trans-10, trans-12 CNA, trans-11, trans-13 CNA and at least one derivative of an above CNA isomer, said derivative being selected from the group consisting of an ester of CNA, a phospholipid of CNA and a salt of CNA in an amount sufficient to control body fat in the animal.

7. The method of claim 6 wherein the administering step comprises oral administration.

8. The method of claim 6 wherein the administering step comprises intravenous injection.

9. The method of claim 6 wherein the administering step comprises direct injection into adipose tissue.

10. The method of claim 6 wherein the administering step comprises topical treatment of skin.

11. The method of claim 6 wherein the ester of CNA is a glyceride.

12. The method of claim 11 wherein the glyceride is selected from the group consisting of a triglyceride of CNA, a diglyceride of CNA, and a monoglyceride of CNA.

* * * * *